US012667401B2

(12) United States Patent
Spliethoff et al.

(10) Patent No.: US 12,667,401 B2
(45) Date of Patent: Jun. 30, 2026

(54) ORTHOPEDIC PIN FOR OPTICALLY ANALYZING A BONE REGION

(71) Applicant: KONINKLIJKE PHILIPS N.V., Eindhoven (NL)

(72) Inventors: Jarich Willem Spliethoff, Utrecht (NL); Bernardus Hendrikus Wilhelmus Hendriks, Eindhoven (NL); Manfred Müller, Eindhoven (NL); Gerhardus Wilhelmus Lucassen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 770 days.

(21) Appl. No.: 17/918,143

(22) PCT Filed: Apr. 19, 2021

(86) PCT No.: PCT/EP2021/060058
§ 371 (c)(1),
(2) Date: Oct. 11, 2022

(87) PCT Pub. No.: WO2021/213967
PCT Pub. Date: Oct. 28, 2021

(65) Prior Publication Data
US 2023/0134673 A1 May 4, 2023

(30) Foreign Application Priority Data

Apr. 23, 2020 (EP) ..................................... 20171068

(51) Int. Cl.
*A61B 17/86* (2006.01)
*A61B 5/00* (2006.01)
(Continued)

(52) U.S. Cl.
CPC .......... *A61B 17/864* (2013.01); *A61B 5/0053* (2013.01); *A61B 5/0075* (2013.01); *A61B 5/4504* (2013.01);
(Continued)

(58) Field of Classification Search
CPC ....... A61B 5/4504; A61B 5/45; A61B 5/4509; A61B 5/68; A61B 5/6846; A61B 5/0053;
(Continued)

(56) References Cited

U.S. PATENT DOCUMENTS

| | | | |
|---|---|---|---|
| 4,909,589 A | 3/1990 | Morris | |
| 8,953,911 B1 * | 2/2015 | Xu | G02B 6/26 385/12 |

(Continued)

FOREIGN PATENT DOCUMENTS

| | | | |
|---|---|---|---|
| CN | 101791246 A | 8/2010 | |
| WO | 2017055144 A1 | 4/2017 | |
| WO | WO-2018162303 A1 * | 9/2018 | ......... A61B 1/00172 |

OTHER PUBLICATIONS

R. J. Mobbs, P. Sivabalan and J. Li, "Technique, challenges and indications for percutaneous pedicle screw fixation", Journal of Clinical Neuroscience 18 (2011)pp. 741-749.
(Continued)

*Primary Examiner* — Marcela I. Shirsat

(57) ABSTRACT

An orthopedic pin is for optically analyzing a bone region. An optical fiber arrangement extends within an elongate shaft from a distal end to a proximal end. There is a coupling at an intermediate position along the shaft, and the optical fiber arrangement comprises a first portion on one side of the coupling and a second portion on the other side of the coupling. The coupling allows relative rotation between
(Continued)

portions of the shaft at opposite sides of the coupling, while maintaining optical coupling between the first and second portions of the optical fiber.

15 Claims, 5 Drawing Sheets

(51) Int. Cl.

| | |
|---|---|
| *A61B 17/00* | (2006.01) |
| *A61B 17/16* | (2006.01) |
| *A61B 17/56* | (2006.01) |
| *A61B 17/70* | (2006.01) |
| *A61B 17/84* | (2006.01) |
| *A61B 17/88* | (2006.01) |
| *A61B 90/00* | (2016.01) |
| *A61F 2/46* | (2006.01) |

(52) U.S. Cl.
CPC ........... *A61B 5/4509* (2013.01); *A61B 5/4566* (2013.01); *A61B 5/6846* (2013.01); *A61B 5/6876* (2013.01); *A61B 2017/00039* (2013.01); *A61B 2017/00061* (2013.01); *A61B 2017/00066* (2013.01); *A61B 2017/00477* (2013.01); *A61B 17/1697* (2013.01); *A61B 2017/564* (2013.01); *A61B 17/7001* (2013.01); *A61B 17/7005* (2013.01); *A61B 17/7032* (2013.01); *A61B 17/7035* (2013.01); *A61B 17/848* (2013.01); *A61B 17/8897* (2013.01); *A61B 2090/064* (2016.02); *A61F 2/4657* (2013.01); *A61F 2002/4666* (2013.01)

(58) Field of Classification Search
CPC ... A61B 5/4566; A61B 5/6878; A61B 5/0075; A61B 5/0084; A61B 5/0071; A61B 2050/05; A61B 2090/064; A61B 2090/065; A61B 2090/066; A61B 17/7001; A61B 17/70; A61B 17/7005; A61B 17/7032; A61B 17/7035; A61B 17/864; A61B 17/00; A61B 17/848; A61B 17/8897; A61B 17/1697; A61B 2017/564; A61B 2017/00061; A61B 2017/00477; A61B 2017/00066; A61B 2017/00057; A61B 2017/00039; A61F 2/4657; A61F 2002/4666; A61F 2002/4667
USPC .......................... 600/587, 584; 606/102, 323
See application file for complete search history.

(56) References Cited

U.S. PATENT DOCUMENTS

| | | | | |
|---|---|---|---|---|
| 2010/0106025 | A1* | 4/2010 | Sarfaty | ................. G01J 3/0291 600/476 |
| 2018/0153623 | A1 | 6/2018 | Noonan et al. | |
| 2018/0280065 | A1* | 10/2018 | Babic | ................. A61B 17/7032 |
| 2020/0000341 | A1* | 1/2020 | Messerschmidt | .. G02B 23/2469 |

OTHER PUBLICATIONS

International Search Report and Written Opinion of PCT/EP2021/060058, dated May 27, 2021.

* cited by examiner

700

702

704

706

708

ORTHOPEDIC PIN FOR OPTICALLY ANALYZING A BONE REGION

CROSS-REFERENCE TO PRIOR APPLICATIONS

This application is the U.S. National Phase application under 35 U.S.C. § 371 of International Application No. PCT/EP2021/060058, filed on Apr. 19, 2021, which claims the benefit of European Patent Application No. 20171068.8, filed Apr. 23, 2020. This application is hereby incorporated by reference herein.

FIELD OF THE INVENTION

The invention relates to an orthopedic pin for optically analyzing a bone region. A related surgical tool and a kit are also disclosed. The invention finds application in the general field of orthopedic surgery, and more particularly in the field of spine surgery. In the latter, the orthopedic pin may for example be used to guide the placement of a pedicle screw.

BACKGROUND OF THE INVENTION

In many medical procedures an implantable device is inserted into bone tissue. For example, bone fixation devices are often used to position bone tissue in relation to other bone tissue or in relation to an external surrounding.

Examples of such medical procedures include pedicle screw insertions in the cervical, thoracic and lumbar spine, fracture fixations in various bone traumas, and plate positioning in hip and knee arthroplasties.

Pedicle screw fixations, as described in a document by Mobbs, R. J., Sivabalan, P., and Li, J., entitled "*Technique, challenges and indications for percutaneous pedicle screw fixation*", Journal of Clinical Neuroscience 18 (2011) pp. 741-749 are a mainstay in the treatment of spinal degenerative disease, intervertebral disc disease, spinal traumas and spinal deformities. Pedicle screw fixation provides short, rigid segmental stabilization that preserves motion segments and stabilizes the spine. Fusion rates and clinical outcome in the treatment of thoracolumbar fractures appear to be superior to that achieved using other forms of treatment. According to a report by the Agency for Healthcare Research and Quality (AHRQ), approximately 488,000 spinal fusions were performed during U.S. hospital stays in 2011 (a rate of 15.7 stays per 10,000 population), which accounted for 3.1% of all operating room procedures.

Despite its worldwide use in enhancing spine stabilization, the safety and effectiveness of pedicle-screw instrumentation has been questioned. A major concerns relates to the accuracy of pedicle screw placement. Pedicle screws are often inserted either blindly or under often-poor fluoroscopic guidance, thus leaving significant room for improvement.

In this respect, document WO 2017/055144 A1 describes a system for implanting an implantable device in bone tissue, a processing unit for such system, a method of implanting an implantable device and a method of providing information for an implanting of an implantable device. In view of the finding that a fat content in cancellous bone is higher than a fat content in compact bone, the lipids fraction, which can be determined by optical means, e.g. spectroscopy, can be used to determine correct screw placement in healthy bone. In one embodiment, document WO 2017/055144 A1 describes a pedicle screw with a hollow shaft, and into which an optical stylet may be inserted. The optical stylet extends to the distal tip of the screw and includes an optical fiber that is used to make optical measurements at the distal tip of the screw. The fat content of the (bone) tissue in front of the tip of the screw is determined via spectroscopic analysis and used to determine whether the (bone) tissue is that of the soft(er) part of the bone or the hard(er) part of the bone to assist in placing the screw. Document WO 2017/055144 A1 also discloses that the optical sensing part may be integrated in a Kirschner wire, i.e. a K-wire, in procedures that involve the initial placement of a K-wire in the bone.

In current solutions, the screw driver and the spectral tissue sensing system are separate devices. Hence, a coupling needs to be made between the, and this is not optimal. In most practical pedicle screw placement procedures, the K-wire is placed first into the vertebrae and in the second step the hollow pedicle screw is inserted (back-loaded) over this K-wire. Typically, a mechanical rotating placement tool (for instance cannulated drill) is used to place the K-wire. Since the smart K-wire is equipped with one or more fibers that need to be connected a console (Optical Spectroscopy Unit; OSU) that emits and receives the reflected light and processes the reflected light, there is a problem of how to connect this OSU to the K-wire while still allowing free rotation of the K-wire.

Furthermore, when employing different tools, a modular approach would be preferred such that a significant part of the screw placement system can be reused i.e. some parts of the cabling can be reconnected to another tool of the screw placement system.

There is therefore a need for an improved surgical tool system.

SUMMARY OF THE INVENTION

The invention is defined by the claims.

The invention provides an orthopedic pin for optically analyzing a bone region, the orthopedic pin comprising:

an elongate shaft having a distal end for insertion into bone, and a proximal end for connection to an analysis unit;

an optical fiber arrangement extending within the elongate shaft from the distal end to the proximal end of the elongate shaft, for transmitting optical radiation from the analysis unit to the bone region and for transmitting reflected optical radiation from the bone region to the analysis unit, when the distal end is inserted into the bone region; and a mechanical and optical coupling at an intermediate position along the shaft, wherein the optical fiber arrangement comprises a first portion on one side of the coupling and a second portion on the other side of the coupling, each for transmitting both the transmitted optical radiation and the reflected optical radiation, and wherein the coupling allows relative rotation between portions of the shaft and the portions of the optical fiber arrangement at opposite sides of the coupling, while maintaining optical coupling between the first and second portions of the optical fiber arrangement.

In other words, the coupling allows relative rotation between portions of the shaft at opposite sides of the coupling and allows relative rotation between the portions of the optical fiber arrangement at opposite sides of the coupling, while maintaining optical coupling between the first and second portions of the optical fiber arrangement. The term "optical fiber arrangement" is intended to cover any elongate optical waveguide system, and hence any light transport structure from one location to another. The term optical fiber should be understood accordingly as indicating any suitable optical waveguide where an optical waveguide is any physical structure that guides electromagnetic waves in the optical spectrum. Common types of optical fiber arrangements include but are not limited to optical fibers and transparent dielectric waveguides made of plastic and glass. Optical fiber arrangements and optical waveguides can have many geometries or shapes such as e.g. planar, strip, or beams such as with cylindrical.

The term "optical" is intended to cover at least a wavelength range typically of 300 nm to 2500 nm. In an embodiment it covers a wavelength range of 400 nm to 1600 nm. A preferred range is from 1000 nm to 1600 nm. This is beneficial for bone type detection because a strong fat absorption takes place around 1200 nm that may help to discriminate cancellous bone (fatty) from cortical bone (non-fatty). Optical may refer to only the visible light spectrum including or excluding the UV spectrum. This orthopedic pin allows rotation of one optical fiber portion relative to the other. In this way, the distal part may be rotated, for example during insertion of the shaft into the bone by drilling or screwing or (rotational) hammering, while the other fiber portion remains rotationally stationary, for example relative to the analysis unit. This simplifies the required connection between the shaft and the analysis unit.

The coupling preferably enables a detachable coupling between the first and second portions. In this way, the distal portion of the shaft may be handled and used separately in conventional manner, for example as a K-wire, without using the optical fiber functionality.

The proximal end of the orthopedic pin is for example able to be slideably received within a channel of a surgical device such as a bone drill bit, a surgical hammer, or a bone fixation device such as a pedicle screw, without the need to modify the surgical device. By way of example, in a first stage of a pedicle screw insertion procedure, a pilot hole may be provided in a bone region by hammering the orthopedic pin into the bone region using a surgical hammer. In a second stage of the pedicle screw insertion procedure a pedicle screw may be slid over the distal end of the orthopedic pin, which serves as a guide. In the first stage the orthopedic pin is received in a channel of the surgical hammer, and during its insertion the bone region is optically analyzed by an optical system coupled to the orthopedic pin.

The end of the optical fiber arrangement at the proximal end is for example configured for a non-rotating coupling to the analysis unit. Not only does this simplify the connection, but it allows the analysis unit to be more remote, for example outside the working field of the physician.

The coupling may have a discrete set of angular orientations between the opposite sides. These enable accurate alignment between fiber ends.

The optical fiber arrangement may comprise a first optical fiber assembly for optical transmission from the optical analysis unit to the distal end and a second optical fiber assembly for optical transmission from the distal end of the elongate shaft to the optical analysis unit.

Thus, different paths are provided for the emitted interrogation light and the reflected detection light.

In a first set of examples, one of the first and second optical fiber assemblies extends along a central axis of the elongate shaft, and the other of the first and second optical fiber assemblies extends offset from the central axis. Thus, there is a concentric arrangement of optical fibers.

The other of the first and second optical fiber assemblies may comprise a single optical fiber at one side of the coupling and an annular ring of optical fibers at the other side of the coupling. Thus, different rotational positions will align the single optical fiber with one from the annular ring.

In another set of examples, the optical fiber arrangement comprises a dual core optical fiber comprising a central core and an outer core, wherein one of the central core and the outer core is for optical transmission from the optical analysis unit to the distal end and the other of the central core and the outer core is for optical transmission from the distal end of the elongate shaft to the optical analysis unit.

This defines another concentric arrangement, using a dual core fiber. There are various options for the use of the dual core fiber.

One option is that the dual core fiber is at one side of the coupling, and an annular ring of fibers is at the other side of the optical coupling.

Another option is that the dual core fiber is at one side of the coupling, and a single non-central optical fiber is at the other side of the optical coupling.

A further option is that there is a dual core fiber at each side of the coupling.

For these concentric arrangements, the optical fiber arrangement may comprise:

at the one side of the coupling, an outer optical fiber arrangement comprising one or more non-central optical fibers or an outer core of a dual core optical fiber;

at the other side of the coupling, a central optical fiber; and a lens for focusing light from the outer optical fiber arrangement to the central optical fiber.

The central optical fiber then functions as a bidirectional optical signal conductor. There may then be a fiber splitter to separate the two signals.

The invention also provides a surgical tool comprising:

the orthopedic pin as defined above; and the optical analysis unit for connection to the proximal end of the elongate shaft.

The optical analysis unit for example comprises an optical source and an optical detector coupled to the optical fiber arrangement.

In one example, the optical analysis unit comprises a spectrometer having the optical detector and a processor, wherein the optical source is for generating optical radiation for irradiating the bone region via the optical fiber arrangement, and optical radiation reflected or scattered by the bone region is optically coupled to the optical detector via the optical fiber arrangement, wherein the processor is configured to:

cause the optical source to generate the optical radiation for optically irradiating the bone region;

receive electrical signals generated by the at least one optical detector in response to optically irradiating the bone region;

process the received electrical signals with an algorithm configured to:

determine at least a first parameter indicative of a fat content or a water content in the bone region based on the received electrical signals; and identify a type of the bone region based on the at least a first parameter; the type being at least one of cancellous bone and cortical bone.

The surgical tool may further comprise:

a pedicle screw, having a central channel for receiving the elongate shaft; and a hollow drill having a channel configured to receive the orthopedic pin; and/or

a surgical screwdriver having a channel configured to
   receive the orthopedic pin; and/or
a surgical hammer having a channel configured to
   receive the orthopedic pin.
   According to further embodiments, there is disclosed the
use of the pin and/or surgical tool within an interventional
method wherein the pin is inserted into a subject.

BRIEF DESCRIPTION OF THE FIGURES

For a better understanding of the invention, and to show
more clearly how it may be carried into effect, reference will
now be made, by way of example only, to the accompanying
drawings, in which.

Figure 1:
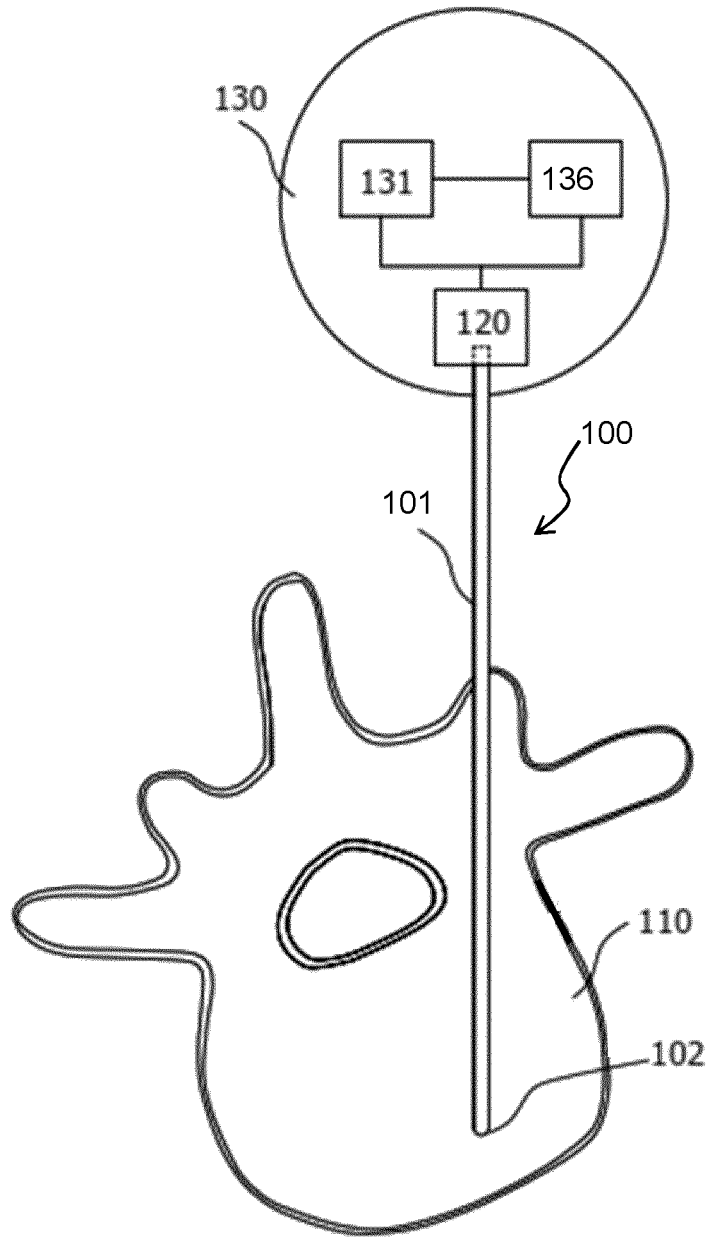
FIG. 1 illustrates a handheld surgical tool in the form of
an analysis unit comprising an optical adapter, a spectrom-
eter and a processor.

DETAILED DESCRIPTION OF THE
INVENTION

The invention will be described with reference to the
Figures.
   It should be understood that the detailed description and
specific examples, while indicating exemplary embodiments
of the apparatus, systems and methods, are intended for
purposes of illustration only and are not intended to limit the
scope of the invention. These and other features, aspects,
and advantages of the apparatus, systems and methods of the
present invention will become better understood from the
following description, appended claims, and accompanying
drawings. It should be understood that the Figures are
merely schematic and are not drawn to scale. It should also
be understood that the same reference numerals are used
throughout the Figures to indicate the same or similar parts.
   The invention provides an orthopedic pin for optically
analyzing a bone region. An optical fiber arrangement
extends within an elongate shaft from a distal end to a
proximal end. There is a coupling at an intermediate position
along the shaft, and the optical fiber arrangement comprises
a first portion on one side of the coupling and a second
portion on the other side of the coupling. The coupling
allows relative rotation between portions of the shaft at
opposite sides of the coupling, while maintaining optical
coupling between the first and second portions of the optical
fiber.
   In order to illustrate the principles of the present invention
an orthopedic pin is described with particular reference to a
medical procedure involving the insertion of a bone fixation
device in the form of a pedicle screw. Reference is made to
an orthopedic pin in the specific form of a K-wire, this type
of orthopedic pin being used routinely in spinal surgery field
to provide, by hammering, and subsequently guide, by being slideably received within the channel of a hollow pedicle
screw, the insertion of the pedicle screw.
   It is however to be appreciated that the invention also
finds application in other medical procedures than the inser-
tion of a bone fixation device, including for example the
insertion of a bone implantable device in general. The term
orthopedic pin refers in general to an elongate device used
fix bone elements or to guide a surgical tool for use in spinal
or orthopedic surgery. Thus, the invention also finds appli-
cation in other types of orthopedic pins than a K-wire,
including but not limited to a Steinmann pin and a trocar.
   Moreover, it is to be appreciated that the orthopedic pin
finds application in guiding the insertion of surgical devices
in general into bone, including but not limited to surgical
devices such as a surgical drill bit, a surgical hammer, a
screwdriver, a dilator and an awl, as well as other bone
fixation devices than a pedicle screw, such as bone screws in
general. Thus, it is contemplated that the orthopedic pin may
be used to guide the insertion of medical devices in general
into bone regions in general, and its application is not
limited to surgical interventions involving the spine.
   The intended use of the orthopedic pin will first be
explained with reference to FIGS. 1 to 3, before the features
in accordance with the invention are described.
   As described in the document by Mobbs, R. J., Sivabalan,
P., and Li, J., entitled "Technique, challenges and indications
for percutaneous pedicle screw fixation", Journal of Clinical
Neuroscience 18 (2011) pp. 741-749, one process for the
percutaneous insertion of a pedicle screw involves the
following steps:
   (i) Place an intra-operative radiography image intensifier
      in the anterior/posterior position. The spinous process
      should be midline between the pedicles to ensure a
      direct anterior/posterior projection.
   (ii) Mark the position of the lateral aspect of the pedicle
      on the skin. Depending upon the depth of the tissue
      between skin and pedicle, the skin incision should be
      made laterally so that a Jamshidi needle can be angled
      appropriately when inserting it into the pedicle.
   (iii) Place the Jamshidi needle through the skin incision
      and "dock" onto the lateral aspect of the pedicle.
   (iv) Advance the Jamshidi needle 20 mm to 25 mm into
      the pedicle, making sure the needle remains lateral to
      the medial pedicle wall.
   (v) Position the intra-operative radiography image inten-
      sifier in the lateral plane. The Jamshidi needle should
      now be in the vertebral body, and therefore "safe" with
      no risk of medial pedicle breach.
   (vi) Place a K-wire down the Jamshidi needle and place
      a pedicle tap down the trajectory of the K-wire.
   (vii) Place the final pedicle screw with the screw placed
      down the K-wire, making sure not to advance the
      K-wire beyond the anterior aspect of the vertebral body.
   In the above-described method the goal of the surgeon is
to ultimately locate the pedicle screw in the relatively softer
core tissue of the vertebra termed "cancellous bone" as
compared to in the relatively harder shell portion of the
vertebra, termed "cortical bone". Serious medical compli-
cations may arise if the surgeon inadvertently punctures the
cortical bone, i.e. "breaches" the pedicle, particularly just
after initially entering the pedicle and whilst navigating
along the neck of the pedicle, as well as at the anterior aspect
of the vertebral body.
   The above-described method of placing a pedicle screw
relies heavily on the use of intra-operative radiography
images in order to avoid these hazards, and suffers from the
continual need to adjust the orientation of the X-ray imaging system. It also suffers from the additional hazard of X-ray dose to the patient and physician.

In the present invention, an orthopedic pin is provided that may be used to improve the guidance of the placement of a pedicle screw using the above-described and other related medical procedures. As mentioned above, the inventive orthopedic pin may be provided in the form of a K-wire, which may take the place of the K-wire described in the above steps in order to guide the subsequent placement of the pedicle screw. As described in more detail below; the inventive K-wire may in general be used in combination with various surgical tools to provide a properly-oriented pilot hole that ultimately allows for the subsequent insertion of a pedicle screw or other bone implant.

FIG. 1 shows a hand held surgical tool 130 in the form of an analysis unit comprising an optical adapter 120, a spectrometer 131 and a processor 136. The analysis unit connects to an orthopedic pin 100 comprising an elongate shaft 101 with a distal end 102.

The spectrometer 131 includes at least one optical light source (not illustrated) and at least one optical detector (not illustrated). The at least one optical source and the at least one optical detector are optically coupled to the optical adapter 120 and arranged such that when the orthopedic pin 100 is received within a port of the optical adapter 120, and when the distal end 102 of the elongate shaft 101 of the orthopedic pin 100 is inserted into bone region 110, optical radiation generated by the at least one optical source irradiates bone region 110 via an optical fiber arrangement of the orthopedic pin (described below), and optical radiation reflected or scattered by the bone region 110 is optically coupled to the at least one optical detector via the optical fiber arrangement.

The orthopedic pin may be provided as part of a kit that includes a surgical device.

Figure 2:
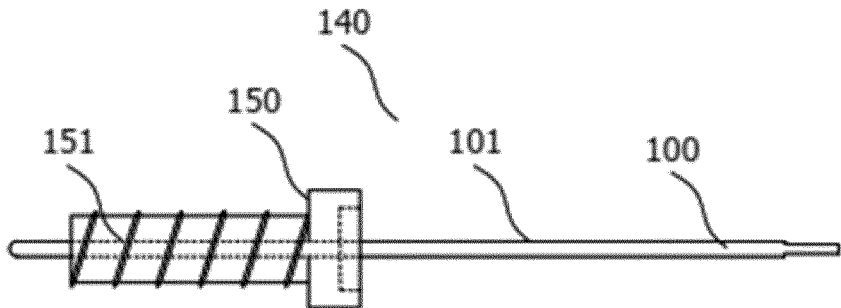
FIG. 2 illustrates a kit including an orthopedic pin
received within a channel of a pedicle screw.

FIG. 2 shows an example of kit which comprises an orthopedic pin 100 and a pedicle screw 150, wherein the pedicle screw comprises a channel 151 for receiving the elongate shaft 101 of the orthopedic pin 100.

Figure 3:
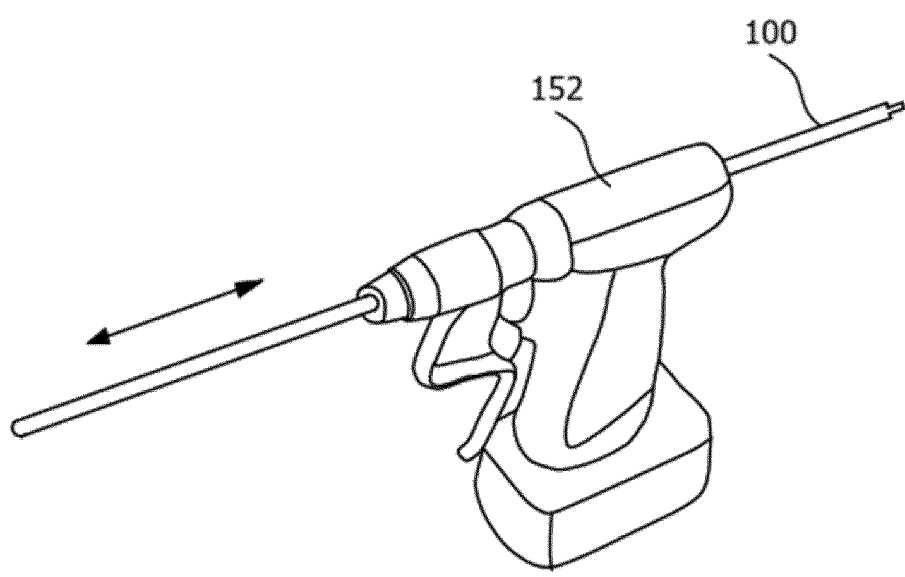
FIG. 3 illustrates another kit including an orthopedic pin
received within a channel of a surgical hammer.

FIG. 3 illustrates another kit 140 including an orthopedic pin 100 received within a channel of a surgical hammer 152.

In another example, a kit may include an orthopedic pin and a hollow drill having a channel configured to receive the orthopedic pin. In another example a kit may include an orthopedic pin and a surgical screwdriver having a channel configured to receive the orthopedic pin. The provision of an orthopedic pin with a surgical tool that combines hammering and drilling and screwing functions is also contemplated.

Figures 4, 5:
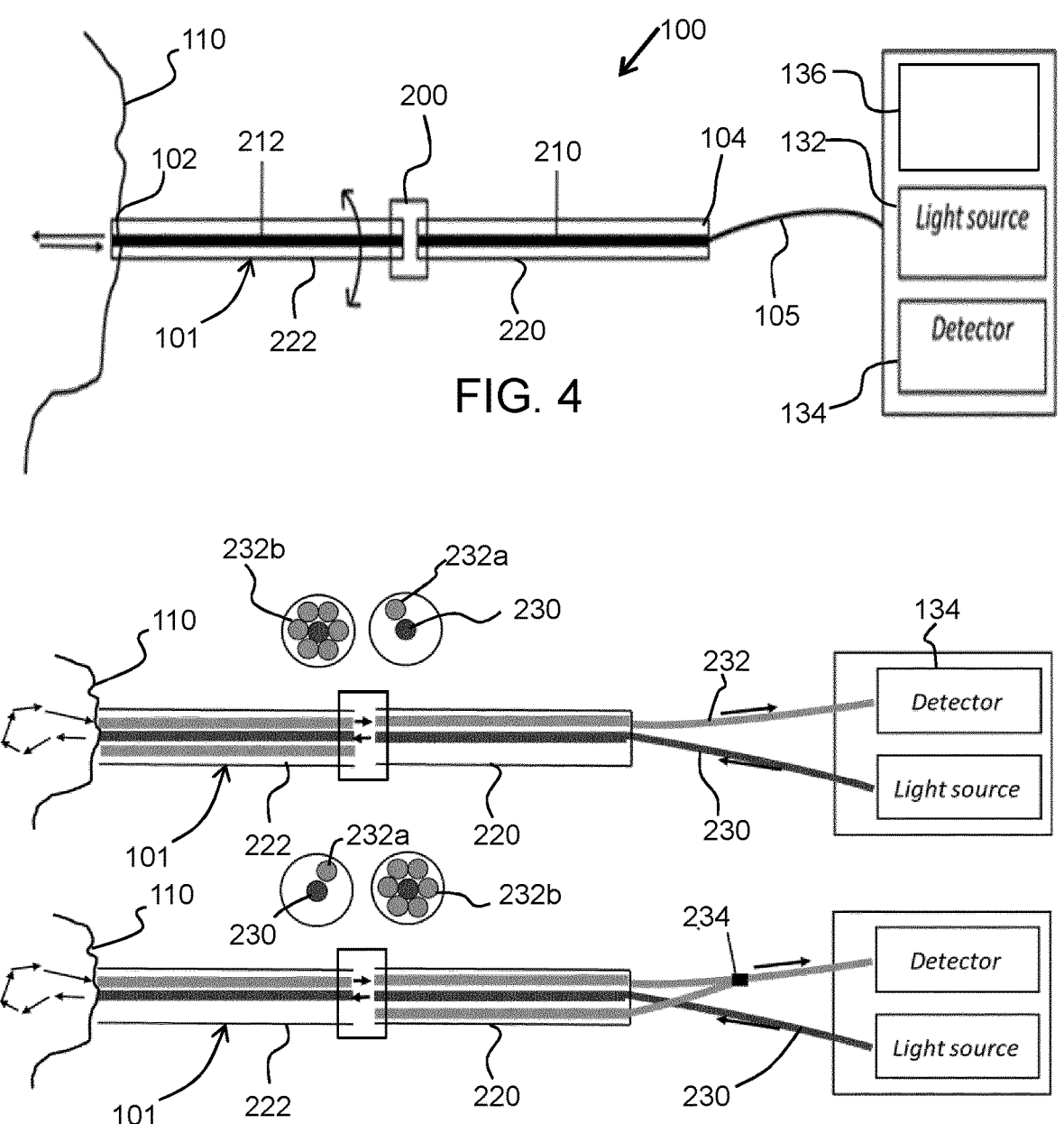
FIG. 4 shows the modification to the orthopedic pin in
accordance with the invention.
FIG. 5 shows a first pair of examples in more detail.

FIG. 4 shows the modification to the orthopedic pin in accordance with the invention.

FIG. 4 shows an orthopedic pin 100 for optically analyzing a bone region.

The orthopedic pin comprises an elongate shaft 101 having a distal end 102 for insertion into bone 110, and a proximal end 104 for connection to an analysis unit 130. The analysis unit has a light source 132, a light detector 134 and a processor 136.

There is an optical fiber arrangement 105 extending within the elongate shaft between the distal end 102 to the proximal end 104 of the elongate shaft, for transmitting optical radiation between the analysis unit 130 and the bone region 110 when the distal end is inserted into the bone region.

A coupling 200 is provided at an intermediate position along the shaft (i.e. between the distal end and the remote end). The optical fiber arrangement comprises a first portion 210 on one (proximal) side of the coupling and a second portion 212 on the other (distal) side of the coupling 200. The elongate shaft 101 has a first portion 220 on one (proximal) side of the coupling and a second portion 222 on the other (distal) side of the coupling. The coupling 200 allows relative rotation between portions 220, 222 of the shaft 101 at opposite sides of the coupling 200, while maintaining optical coupling between the first and second portions 210, 212 of the optical fiber.

This orthopedic pin allows rotation of one optical fiber portion relative to the other. In this way, the distal part may be rotated, for example during insertion of the shaft into the bone by drilling or screwing or (rotational) hammering, while the other fiber portion remains rotationally stationary, for example relative to the analysis unit 130. This simplifies the required connection between the proximal part 220 of the shaft and the analysis unit 130.

The coupling is detachable so that the distal portion 222 of the shaft may be handled and used in conventional manner, for example as a K-wire, without using the optical fiber functionality. Thus, before there is a coupling formed, the K-wire can be used as a "regular" k-wire, allowing cannulated instruments/screws to be slid over the wire from the proximal end (back-loading). Once a connection is established between the analysis unit and the K-wire, spectral tissue sensing can be performed. The connection is reversible so the connection-disconnection can be repeated several times.

The end of the optical fiber arrangement at the proximal end is for example configured for a non-rotating coupling to the analysis unit 130. This simplifies the connection, but it allows the analysis unit to be more remote, for example outside the working field of the physician. The analysis unit does not then need to be miniaturized.

FIG. 5 shows a first pair of examples in more detail.

The optical fiber arrangement 105 has a first optical fiber assembly 230 for optical transmission from the optical analysis unit 130 to the distal end 102 and a second optical fiber assembly 232 for optical transmission from the distal end 102 of the elongate shaft to the optical analysis unit 130. Thus, different paths are provided for the emitted interrogate light and the reflected detection light.

In the example of FIG. 5, the first optical fiber assembly 230 extends along a central axis of the elongate shaft 101 (parts 220 and 222) and comprises a single optical fiber. The second optical fiber assembly 232 extends offset from the central axis. Thus, there is a concentric arrangement of optical fibers.

The second optical fiber assembly 232 comprises a single optical fiber 232a at one side of the coupling and an annular ring 232b of optical fibers at the other side of the coupling.

In the top part of FIG. 5, the single optical fiber 232a is at the proximal side whereas in the bottom part of FIG. 5, the single optical fiber 232a is at the distal side. A fiber splitter 234 combines the signals from the multiple fibers of the annular ring for the detector.

The coupling may then have a discrete set of angular orientations between the opposite sides. These enables accurate alignment between fiber ends, in particular between the fiber end of the single optical fiber 232a and one of the fibers of the annular ring 232b.

The fiber endings at the distal end are preferably located with a distance from each other greater than the diameter of the fibers. With such an arrangement of the fibers, especially diffuse reflectance spectroscopy is possible with good results.

The direction of light travel in FIG. 5 may be reversed (i.e. the central fiber may be used for the reflected light and the offset fibers may be used for the delivered light).

Figure 6:
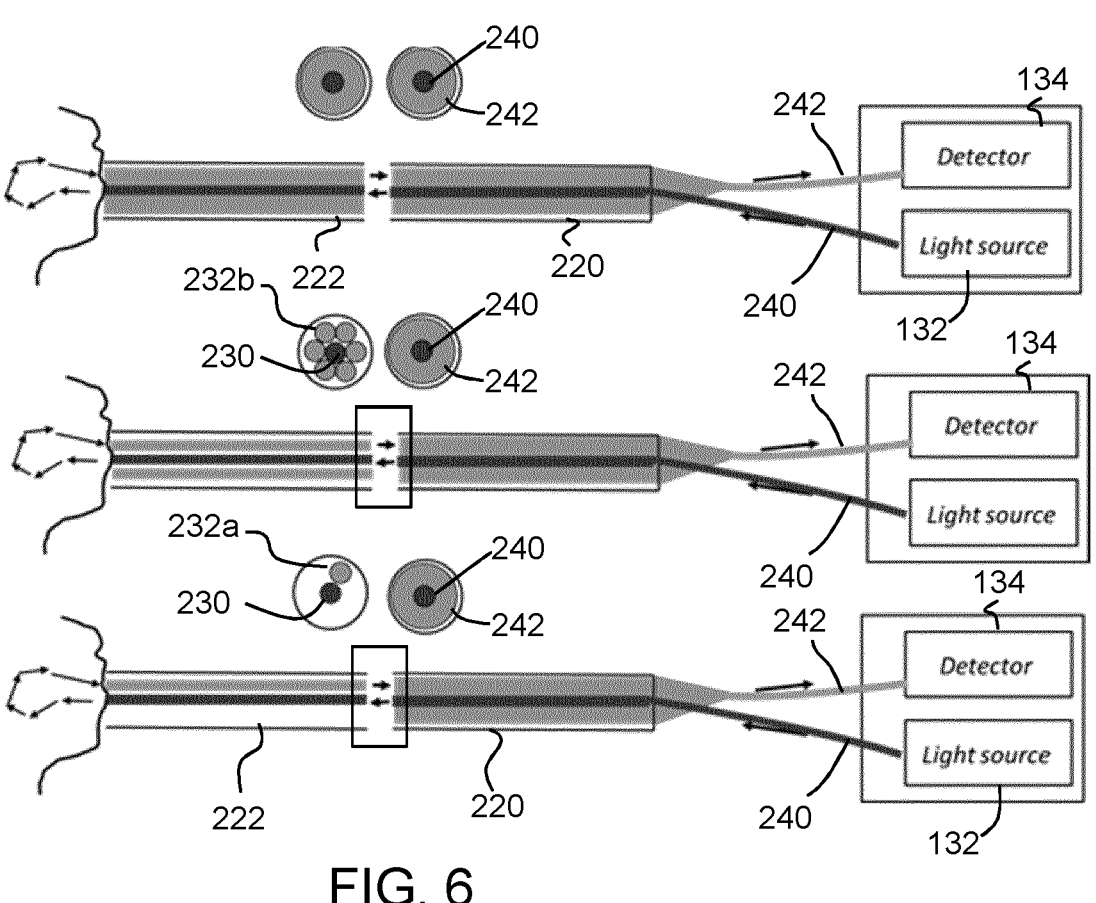
FIG. 6 shows another set of examples which make use of
one or more dual core optical fibers.

FIG. 6 shows another set of examples which make use of one or more dual core optical fibers, comprising a central core 240 and an outer core 242.

One of the central core and the outer core is used for optical transmission from the optical analysis unit to the distal end and the other of the central core and the outer core is for optical transmission from the distal end of the elongate shaft to the optical analysis unit.

The examples of FIG. 6 use the central core for delivery of the light source light and the outer core for the reflected light. The opposite is possible.

The top image shows a dual core fiber at each side of the coupling.

The middle image shows the dual core fiber 240, 242 at one side (the proximal side) of the coupling, and an annular ring 232b of fibers around a central fiber 230 is at the other side of the optical coupling.

The bottom image shows the dual core fiber 240, 242 is at one side of the coupling, and a single non-central optical fiber 232a is at the other side of the optical coupling, offset from a central fiber 230.

Lenses may be used to couple light from outer fibers to a central fiber.

Figure 7:
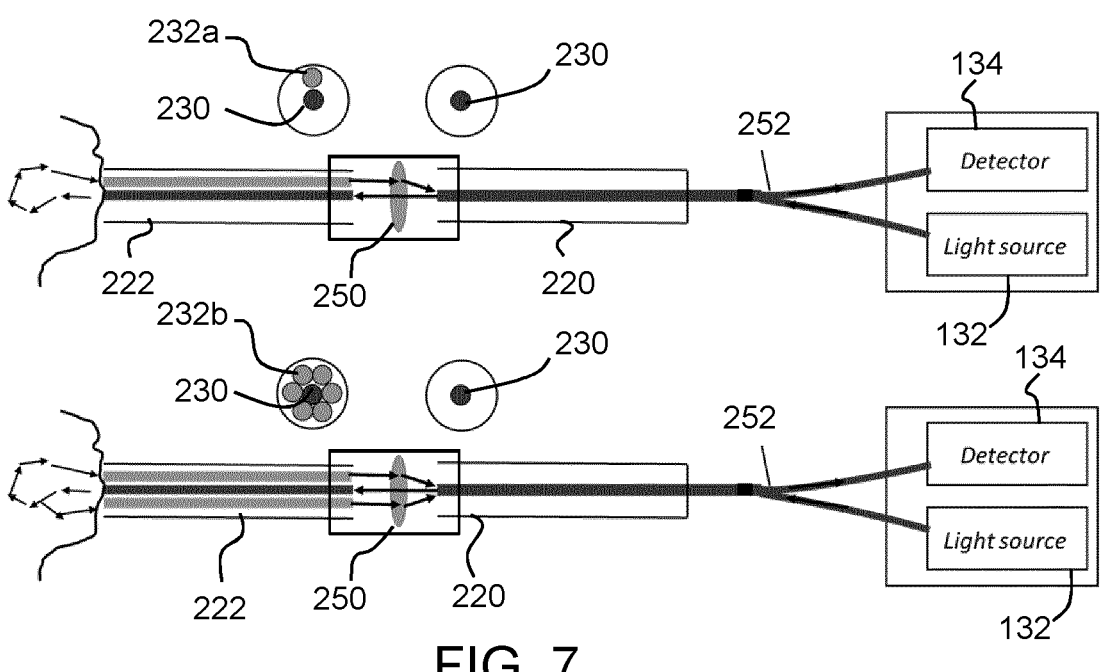
FIG. 7 shows another set of examples making use of a
lens.
Figure 8:
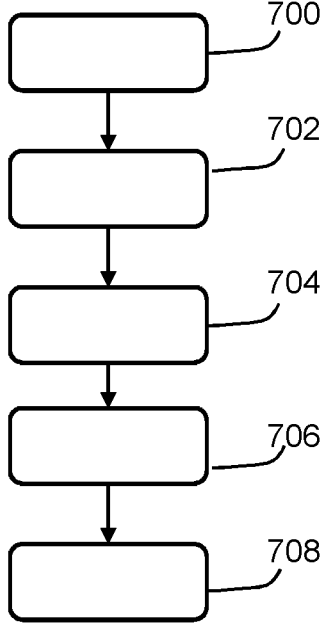
FIG. 8 shows a method which may be performed by
processor of the analysis unit.

FIG. 7 shows an optical fiber arrangement comprising, at one (distal) side of the coupling, an outer optical fiber arrangement comprising one non-central optical fiber 232a (top image) or an annular ring of non-central optical fibers 232b (bottom image), in both cases around a central optical fiber 230.

At the other side of the coupling there is only a central optical fiber 230.

A lens 250 is provided for focusing light from the outer optical fiber arrangement to the central optical fiber.

The central optical fiber 230 then functions as a bidirectional optical signal conductor. There may then be a fiber splitter 252 to separate the two signals returning to the analysis unit 130.

This approach may be applied to a dual core fiber as well. Again, the single core fiber could instead be at the distal side and the concentric arrangement could be at the proximal side.

FIG. 7 shows a method which may be performed by processor 132 of the analysis unit.

In step 700, the optical source is operated to generate the optical radiation for optically irradiating the bone region 110.

In step 702, the electrical signals generated by the at least one optical detector are received, in response to optically irradiating the bone region 110.

In step 704, the received electrical signals are analyzed to determine at least a first parameter indicative of a fat content or a water content in the bone region 110 based on the received electrical signals.

In step 706, the analysis identifies a type of the bone region 110 based on the at least a first parameter; the type being at least one of cancellous bone and cortical bone.

Optionally the algorithm may be further configured to determine at least a second parameter indicative of a collagen content and/or optical scattering in the bone region 110 and identify the type of the bone region 110 based further on the at least a second parameter.

The inclusion of collagen and/or optical scattering in the analysis may further improve the discrimination between cortical bone and cancellous bone.

Moreover, the algorithm may be further configured to determine a blood content in the bone region 110.

The surgical tool may further comprise an indicator; wherein the indicator is configured to generate a first output if the type of the bone region 110 is cancellous bone and a second output if the type of the bone region 110 is cortical bone 110b. A third output indicative of a certainty of the identification of the type of the bone region 110 may also be provided based on the determined blood content in the bone region 110.

The certainty of the identification of the type of the bone region has been found to inversely correlate with blood content. This is because if the orthopedic pin is inserted into a bone region and then withdrawn slightly, the resulting void between the distal end of the orthopedic pin and the bone region tends to be filled with blood. The optical signal may be unreliable due to the absence of contact between the distal end and the bone region. Thus, if blood is detected in the optical signal it may be indicative of an unreliable signal.

A technique for optically analyzing the bone region 110 based on optical radiation diffusely reflected from the bone region in order to determine the aforementioned optical parameters as delivered by optical fiber(s) 105 is described in a document by R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm", Optics Express, vol. 18, 2010, pp. 879-888, and a document by R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", Journal of Biomedical Optics, vol. 15, May 2010, pp. 037015-10. From these diffuse reflectance spectroscopy, i.e. DRS, measurements, tissue transitions can be deduced, wherein furthermore specifically a parameter indicative of a fat content of the tissue can be obtained.

Although diffuse reflectance spectroscopy is described above to extract tissue properties, other optical methods can also be envisioned, including diffuse optical tomography by employing a plurality of optical fibers, differential path length spectroscopy, fluorescence and Raman spectroscopy. Additionally, acquisition of optical data could be done via a probe that is contact with the tissue or via a non-contact probe.

In order to determine whether a certain tissue is in front of the optical fiber(s), the DRS signal can be compared with a look-up-table. Another way is to translate the measured parameters into physiological parameters and define ranges for these parameters for each tissue type. Incorporating referral is made to Duck, F. A., "Physical properties of tissue: A comprehensive reference book", 1990, Academic Press, Harcourt Brace Jovanovich, Publishers, where methods based on classification and regression tree "CART" analyses are described for classifying tissue based on these physiological parameters.

An example of extracting the physiological parameter is by fitting the acquired spectra using a custom made Matlab 7.9.0, Mathworks, Natick, MA, algorithm. In this algorithm, a widely accepted analytical model was implemented, namely the model introduced by T. J. Farrel, M. S. Patterson and B. C. Wilson, "A diffusion theory model of spatially resolved, steady-state diffuse reflectance for the non-invasive determination of tissue optical properties", Med. Phys. 19 (1992) p. 879-888. The input arguments for the model of Farrel et al. are the absorption coefficient $\mu_a(\lambda)$, the reduced scattering coefficient $\mu_s'(\lambda)$ and the center-to-center distance between the emitting and collecting fibers at the tip of the probe. For a complete description of the diffusion theory model, referral is made to the document of Farrel et al.

In the following, the model will be explained briefly. The formulas are mainly based on the work of Nachabe et al. mentioned above (R. Nachabe, B. H. W. Hendriks, M. V. D. Voort, A. E, and H. J. C. M. Sterenborg, "*Estimation of biological chromophores using diffuse optical spectroscopy: benefit of extending the UV-VIS wavelength range to include 1000 to 1600 nm*", Optics Express, vol. 18, 2010, pp. 879-888, and furthermore reference is made in this context also to R. Nachabe, B. H. W. Hendriks, A. E. Desjardins, M. van der Voort, M. B. van der Mark, and H. J. C. M. Sterenborg, "*Estimation of lipid and water concentrations in scattering media with diffuse optical spectroscopy from 900 to 1600 nm*", Journal of Biomedical Optics, vol. 15, May 2010, pp. 037015-10.

A double power law function can be used to describe the wavelength dependence of the reduced scattering coefficient, where the wavelength $\lambda$ is expressed in nm and is normalized to a wavelength value of $\lambda_0=800$ nm. The parameter a corresponds to the reduced scattering amplitude at this specific wavelength.

$$\mu_s'(\lambda) = a\left(\rho_{MR}\left(\frac{\lambda}{\lambda_0}\right)^{-b} + (1 - \rho_{MR})\left(\frac{\lambda}{\lambda_0}\right)^{-4}\right)\left[cm^{-1}\right] \qquad \text{(Eq. 1)}$$

In this equation the reduced scattering coefficient is expressed as the sum of Mie and Rayleigh scattering where pin is the Mie-to-total reduced scattering fraction. The reduced scattering slope of the Mie scattering is denoted as b and is related to the particle size.

For a homogeneous distribution of absorbers, the total light absorption coefficient $\mu_a(\lambda)$ can be computed as products of the extinction coefficients and volume fraction of the absorbers (see FIG. 17, which illustrates a log plot of the absorption spectra of blood hemoglobin (line 220), oxygenated hemoglobin (line 221), water (line 222) and fat (line 223), with the abscissa indicating the wavelength in nm and the ordinate showing $\mu_a(\lambda)$ in $cm^{-1}$):

$$\mu_a^{Total} = f_1\mu_a^1 + f_2\mu_a^2 + f_3\mu_a^3 + \ldots \qquad \text{(Eq. 2)}$$

Instead of modeling the absorption coefficient $\mu_a(\lambda)$ as the sum of absorption coefficients weighted by the respective concentrations of the four chromophores of interest, it was decided to express the tissue absorption coefficient as:

$$\mu_a^{Tissue}(\lambda) = C(\lambda)v_{Blood}\mu_a^{Blood}(\lambda) + v_{WL}\mu_a^{WL}(\lambda)\left[cm^{-1}\right] \qquad \text{(Eq. 3)}$$

where $$\mu_a^{Blood}(\lambda)$$

corresponds to the absorption by blood and $$\mu_a^{WL}(\lambda)$$

corresponds to absorption by water and lipid together in the probed volume. The volume fraction of water and lipid is $v_{WL}=[\text{Lipid}]+[\text{H}_2\text{O}]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as:

$$C(\lambda) = \frac{1 - \exp\left(-2R\mu_a^{Blood}(\lambda)\right)}{2R\mu_a^{Blood}(\lambda)} \qquad \text{(Eq. 4)}$$

where R denotes the average vessel radius expressed in cm. The absorption coefficient related to blood is given by:

$$\mu_a^{Blood}(\lambda) = \alpha_{BL}\mu_a^{HbO_2}(\lambda) + (1 - \alpha_{BL})\mu_a^{Hb}(\lambda)\left[cm^{-1}\right] \qquad \text{(Eq. 5)}$$

where $$\mu_a^{HbO_2}(\lambda)$$

and $$\mu_a^{Hb}(\lambda)$$

represent the basic extinction coefficient spectra of oxygenated hemoglobin $HbO_2$ and deoxygenated hemoglobin Hb, respectively. The oxygenated hemoglobin fraction in the total amount of hemoglobin is noted as $\alpha_{BL}=[\text{HbO}_2]/([\text{HbO}_2]+[\text{Hb}])$ and is commonly known as the blood oxygen saturation. The absorption due to the presence of water and lipid in the measured tissue is defined as:

$$\mu_a^{WL}(\lambda) = \alpha_{WL}\mu_a^{Lipid}(\lambda) + (1 - \alpha_{WL})\mu_a^{H_2O}(\lambda)\left[cm^{-1}\right] \qquad \text{(Eq. 6)}$$

In this case the concentration of lipid related to the total concentration of lipid and water together can be written as $\alpha_{WF}=[\text{Lipid}]/([\text{Lipid}]+[\text{H}_2\text{O}])$, where [Lipid] and [H$_2$O] correspond to the concentration of lipid (density of 0.86 g/ml) and water, respectively.

This way of relating the water and lipid parameters in the expression of the absorption coefficient is defined in Eq.6, rather than estimating separately the water and lipid volume fraction corresponding to a minimization of the covariance of the basic functions for fitting, thus resulting in a more stable fit (see, also for further explanation and validation of this theorem the above mentioned papers by R. Nachabé et al).

Other optical absorbers could also be incorporated into this algorithm, such as: lycopene, vitamin A, β-carotene, or bile.

Another way to discriminate differences in spectra is by making use of a principal component analysis. This method allows classification of differences in spectra and thus allows discrimination between tissues. It is also possible to extract features from the spectra.

Aside from diffuse reflectance one could also measure fluorescence spectra. Then for instance parameters like collagen, elastin, Nicotinamide adenine dinucleotide in reduced form, i.e. NADH, and Flavin adenine dinucleotide, i.e. FAD could also be measured (see FIG. 18, which illustrates intrinsic fluorescence curves for collagen, elastin, NADH and FAD, with the abscissa providing the wavelength in nm and the ordinate giving the fluorescence intensity in arbitrary units. The ratio NADH/FAD, which is called the optical redox parameter, is of interest because it is an indicator for the metabolic state of the tissue (see M. Müller and B. H. W. Hendriks, "*Recovering intrinsic fluorescence by Monte Carlo modeling*", J. Biomed. Optics vol. 18 (2013) p. 027009-1 to 027009-13, and references therein, which can also be used to discriminate tissues.

It is noted that any of the method steps disclosed herein, particularly those described in relation to processor 132, may be recorded in the form of instructions which when executed on the processor cause the processor to carry out such method steps.

The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk—read only memory "CD-ROM", compact disk—read/write "CD-R/W", Blu-Ray™ and DVD.

The detailed examples described above with reference to FIGS. 5 to 7 all have a concentric arrangement of optical fibers, with different paths in the two directions.

It is instead possible to use a single core fiber for bidirectional optical transmission. As in the examples above, an optical splitter may be used to extract the signal for analysis from the bidirectional fiber. The optical fiber arrangement 105 of FIG. 4 may in such a case be a single optical fiber.

The light source, detector and processor (forming an optical spectroscopy unit) may all be integrated as part of a handheld surgical instrument, i.e. implemented as a detachable knob for attachment to the proximal end of the proximal portion of the elongate shaft and optical fiber arrangement.

Another option is for an optical spectroscopy unit to be integrated with a placement tool such as a drill. The integrated optical spectroscopy unit may be fixed to a stationary part of the placement tool (otherwise extreme miniaturization of the optical spectroscopy unit would be required) and hence at one side of the coupling described above. The rotating drill would then be connected to the rotating fiber-optic K-wire at other side of the coupling described above. The K-wire is then connected to and disconnected from the placement tool at the coupling.

The distal portion of the optical fiber arrangement and the distal portion of the elongate shaft for example have a length below 100 cm, for example in the range 10 cm to 50 cm. The proximal portion of the optical fiber arrangement and the proximal portion of the elongate shaft may be very short, for example if the the analysis unit is part of a handheld tool, and the coupling is at the interface to the handheld tool. If the analysis unit is outside the surgery field, proximal portions may be much longer, for example over 2 m, for example in the range 3 m to 4 m.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. An orthopedic pin for optically analyzing a bone region, the orthopedic pin comprising:

an elongate shaft having a distal end configured to be inserted into bone, a proximal end for connection to an analysis unit, a distal portion of the elongate shaft, and a proximal portion of the elongate shaft;

an optical fiber arrangement extending within the elongate shaft from the distal end to the proximal end of the elongate shaft, for transmitting optical radiation from the analysis unit to the bone region and for transmitting reflected optical radiation from the bone region to the analysis unit, when the distal end is inserted into the bone region; and a mechanical and optical coupling at an intermediate position along the elongate shaft such that the distal portion of the elongate shaft is on one side of the coupling and the proximal portion of the elongate shaft is on the other side of the coupling, wherein the optical fiber arrangement comprises a first portion on one side of the coupling and a second portion on the other side of the coupling, each for transmitting both the transmitted optical radiation and the reflected optical radiation,

15 and wherein the coupling allows relative rotation between the distal portion and the proximal portion of the elongate shaft and relative rotation between the first portion and the second portion of the optical fiber arrangement at opposite sides of the coupling, while maintaining optical coupling between the first and second portions of the optical fiber arrangement.

2. The orthopedic pin of claim 1, wherein the coupling enables a detachable coupling between the first and second portions.

3. The orthopedic pin of claim 1, wherein the end of the optical fiber arrangement at the proximal end is configured for a non-rotating coupling to the analysis unit.

4. The orthopedic pin claim 1, wherein the coupling has discrete set of angular orientations between the opposite sides.

5. The orthopedic pin of claim 1, wherein the optical fiber arrangement comprises a first optical fiber assembly for optical transmission from an optical analysis unit to the distal end and a second optical fiber assembly for optical transmission from the distal end of the elongate shaft to the optical analysis unit.

6. The orthopedic pin of claim 5, wherein one of the first and second optical fiber assemblies extends along a central axis of the elongate shaft, and the other of the first and second optical fiber assemblies extends offset from the central axis.

7. The orthopedic pin of claim 6, wherein said other of the first and second optical fiber assemblies comprises a single optical fiber at one side of the coupling and an annular ring of optical fibers at the other side of the coupling.

8. The orthopedic pin of claim 1, wherein the optical fiber arrangement comprises a dual core optical fiber comprising a central core and an outer core, wherein one of the central core and the outer core is for optical transmission from an optical analysis unit to the distal end and the other of the central core and the outer core is for optical transmission from the distal end of the elongate shaft to the optical analysis unit.

9. The orthopedic pin of claim 8, wherein:
the dual core fiber is at one side of the coupling, and an annular ring of fibers is at the other side of the optical coupling; or
the dual core fiber is at one side of the coupling, and a single non-central optical fiber is at the other side of the optical coupling; or
there is a dual core fiber at each side of the coupling.

10. The orthopedic pin of claim 8, wherein the optical fiber arrangement comprises:
at the one side of the coupling, an outer optical fiber arrangement comprising one or more non-central optical fibers or an outer core of a dual core optical fiber;
at the other side of the coupling, a central optical fiber; and
a lens for focusing light from the outer optical fiber arrangement to the central optical fiber.

11. The orthopedic pin of claim 10, further comprising a fiber splitter for dividing signals from the central optical fiber.

12. A surgical tool comprising:
the orthopedic pin for optically analyzing a bone region, the orthopedic pin comprising:
an elongate shaft having a distal end configured to be inserted into bone, a proximal end for connection to an analysis unit, a distal portion of the elongate shaft, and a proximal portion of the elongate shaft;
an optical fiber arrangement extending within the elongate shaft from the distal end to the proximal end of the elongate shaft, for transmitting optical radiation from the analysis unit to the bone region and for transmitting reflected optical radiation from the bone region to the analysis unit, when the distal end is inserted into the bone region; and
a mechanical and optical coupling at an intermediate position along the elongate shaft such that the distal portion of the elongate shaft is on one side of the coupling and the proximal portion of the elongate shaft is on the other side of the coupling,
wherein the optical fiber arrangement comprises a first portion on one side of the coupling and a second portion on the other side of the coupling, each for transmitting both the transmitted optical radiation and the reflected optical radiation, and
wherein the coupling allows relative rotation between the distal portion and the proximal portion of the elongate shaft and relative rotation between the first portion and the second portion of the optical fiber arrangement at opposite sides of the coupling, while maintaining optical coupling between the first and second portions of the optical fiber arrangement; and
an optical analysis unit for connection to the proximal end of the elongate shaft.

13. The surgical tool of claim 12, wherein the optical analysis unit comprises an optical source and an optical detector coupled to the optical fiber arrangement.

14. The surgical tool of claim 13, wherein the optical analysis unit comprises a spectrometer having the optical detector and a processor, wherein the optical source is for generating optical radiation for irradiating the bone region via the optical fiber arrangement, and optical radiation reflected or scattered by the bone region is optically coupled to the optical detector via the optical fiber arrangement,
wherein the processor is configured to:
cause the optical source to generate the optical radiation for optically irradiating the bone region;
receive electrical signals generated by the at least one optical detector in response to optically irradiating the bone region;
process the received electrical signals with an algorithm configured to:
determine at least a first parameter indicative of a fat content or a water content in the bone region based on the received electrical signals; and to
identify a type of the bone region based on the at least a first parameter; the type being at least one of cancellous bone and cortical bone.

15. The surgical tool of claim 12, further comprising:
a pedicle screw, having a central channel for receiving the elongate shaft; and
a hollow drill having a channel configured to receive the orthopedic pin; and/or
a surgical screwdriver having a channel configured to receive the orthopedic pin; and/or
a surgical hammer having a channel configured to receive the orthopedic pin.

* * * * *